United States Patent [19]
Goodin et al.

[11] Patent Number: 5,980,531
[45] Date of Patent: Nov. 9, 1999

[54] STENT DEPLOYMENT DEVICE WITH TWO BALLOONS

[75] Inventors: Richard L. Goodin, Blaine; Robert E. Burgmeier, Plymouth, both of Minn.

[73] Assignee: Schneider Inc, Plymouth, Minn.

[21] Appl. No.: 08/927,347

[22] Filed: Sep. 11, 1997

[51] Int. Cl.⁶ ..................................................... A61F 11/00
[52] U.S. Cl. ........................................... 606/108; 604/101
[58] Field of Search ..................................... 606/194, 108, 606/192, 198, 191; 604/101

[56] References Cited

U.S. PATENT DOCUMENTS

| | | | |
|---|---|---|---|
| 4,423,725 | 1/1984 | Baran | 128/207.15 |
| 4,744,366 | 5/1988 | Jang . | |
| 4,906,244 | 3/1990 | Pinchuk | 606/194 |
| 4,955,895 | 9/1990 | Sugiyama | 606/194 |
| 5,270,086 | 12/1993 | Hamlin | 428/35.2 |
| 5,505,699 | 4/1996 | Forman et al. . | |
| 5,536,252 | 7/1996 | Imran | 604/101 |

FOREIGN PATENT DOCUMENTS

WO 94/19049  9/1994  WIPO ........................... A61M 29/00
WO 96/38109  12/1996  WIPO ............................ A61F 11/00

OTHER PUBLICATIONS

U.S. application No. 08/916,610, Di Capri et al., filed Aug. 22, 1997.

Primary Examiner—Michael Buiz
Assistant Examiner—Kevin Truong
Attorney, Agent, or Firm—Faegre & Benson LLP

[57] ABSTRACT

A stent delivery device having a pair of balloons at a proximal end of a catheter and having separate lumens for selectively inflating the respective balloons. The outer balloon is relatively compliant and the inner balloon is relatively non-compliant. A central lumen is provided for a guide wire. A stent is carried by the delivery device within an axially retractable sheath at the distal end of the catheter and is deployed by retraction of the sheath and inflation of the compliant balloon, and the stent is subsequently expanded by inflation of the non-compliant balloon.

23 Claims, 6 Drawing Sheets

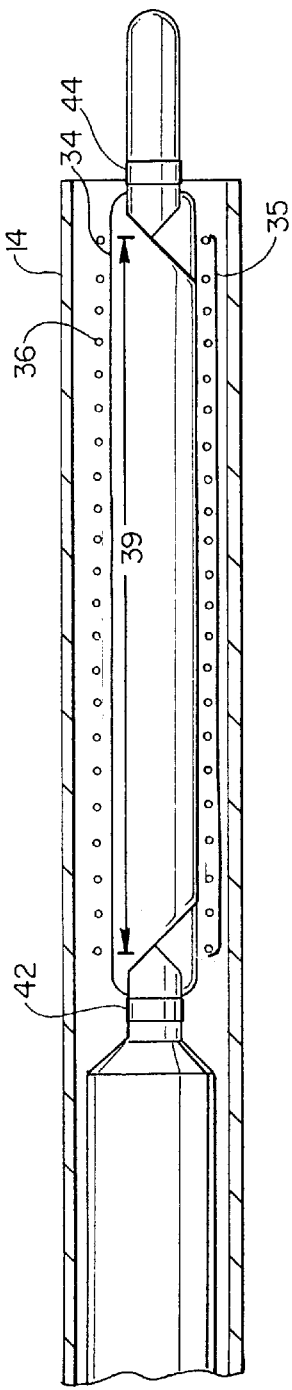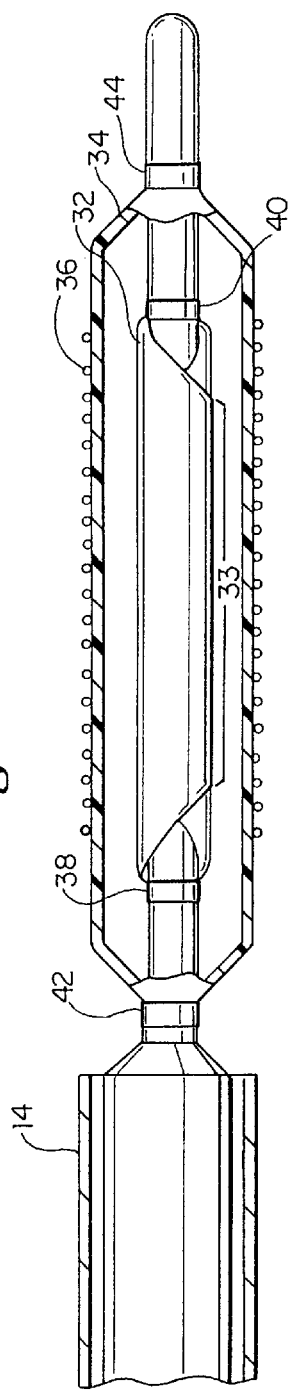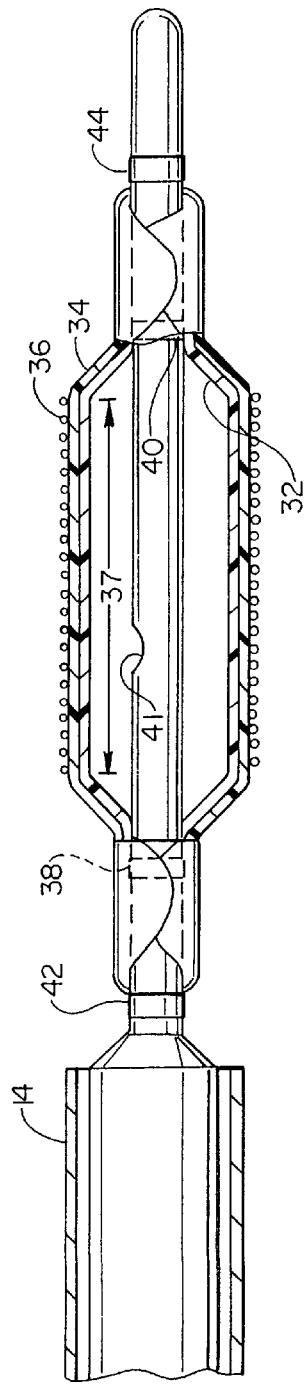

STENT DEPLOYMENT DEVICE WITH TWO BALLOONS

BACKGROUND OF THE INVENTION

This invention relates to the field of stent deployment devices of the type for delivering and deploying a stent to a treatment site in a vessel of a living organism, more particularly, an animal or human. The device of the present invention includes two balloons, one being compliant and used for stent deployment at a relatively low pressure, and the other being non-compliant and available for post-deployment stent expansion at a relatively high pressure.

BRIEF DESCRIPTION OF THE DRAWINGS

FIG. 5 is a simplified section view of the distal end of the apparatus of FIG. 3 shown in an initial condition ready for insertion into a vessel with the outer sleeve shown in section and extended over a stent.

FIG. 6 is a view similar to FIG. 5 except with the outer sleeve retracted and the outer balloon inflated and in section showing stent deployment.

FIG. 7 is a view similar to FIG. 6 except with the inner balloon inflated with parts cut away showing post-deployment stent expansion.

DETAILED DESCRIPTION OF THE INVENTION

Figure 1:
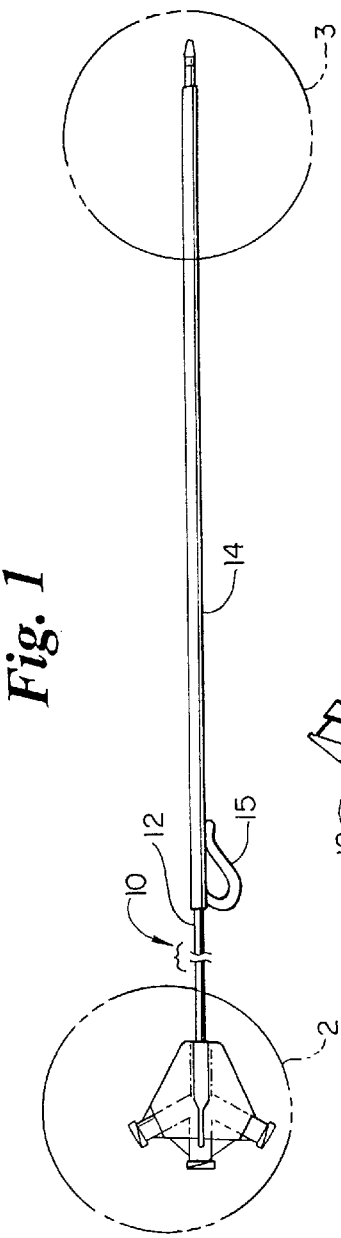
FIG. 1 is an overall view of a stent delivery apparatus useful in the practice of the present invention.
Figure 2:
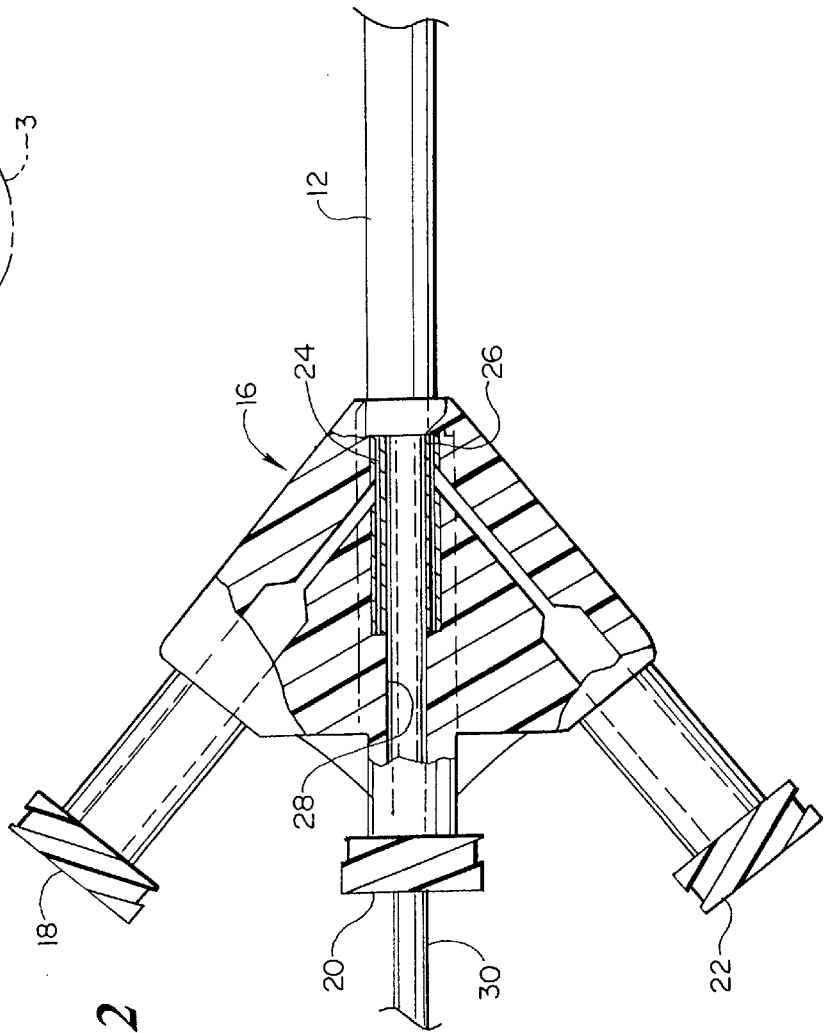
FIG. 2 is an enlarged view partly in section of detail 2 of FIG. 1 showing the manifold-lumen fluid paths at the proximal end.
Figure 3:
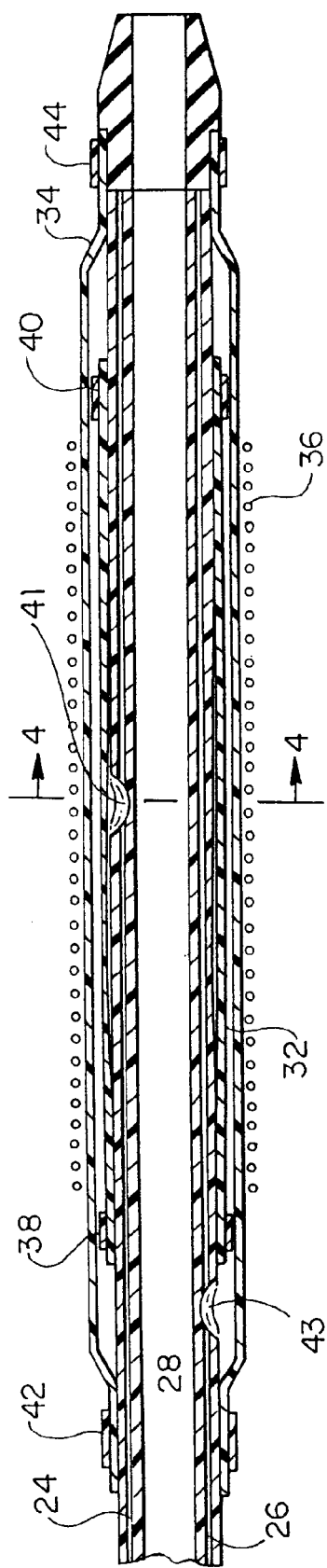
FIG. 3 is an enlarged section view of a distal end of the apparatus of FIG. 1 showing the lumen-balloon fluid paths with the balloons shown in respective deflated conditions with an outer sleeve and guide wire omitted.
Figure 4:
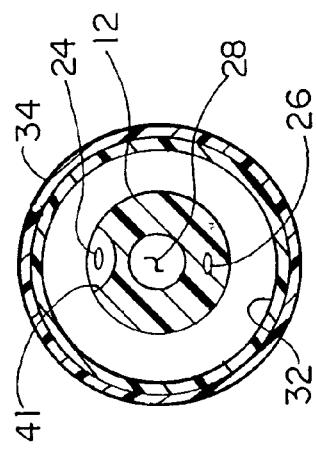
FIG. 4 is a section view along line 4—4 of FIG. 3, except with the inner balloon shown inflated and the stent omitted.

Referring now to the Figures, and most particularly to FIGS. 1, 2 and 3, a stent delivery system or medical device 10 may be seen. System or device 10 includes a three lumen catheter 12 preferably formed of a polymer or combination of polymers such as polyamide, polyester, polyimide, or the like and carries a slidable sleeve 14 on the exterior thereof. System 10 also includes a valve body or manifold 16 preferably formed of a relatively rigid conventional polymer material, such as polycarbonate. Manifold 16 is secured to catheter 12 in a conventional fluid-tight manner and has ports 18, 20, and 22 in communication with respective lumens of catheter 12. Port 18 is in fluid communication with lumen 24; port 22 is in fluid communication with lumen 26; and port 20 is in communication with lumen 28, with port 20 and lumen 28 preferably adapted to receive a conventional guide wire 30. As shown in FIG. 1, outer sleeve 14 extends to a region near the proximal end of assembly 10 and is thus retractable by manipulation of the proximal end of sleeve 14, either directly or through the use of an enlarged portion such as a finger loop 15. Sleeve 14 may be formed of a polyolefin such as polyethylene or polypropylene; a fluorinated polymer such as polytetrafluoroethylene or fluoroethylene propylene; a polyamide such as nylon, or other suitable material, as desired, and may be homogeneous or may be formed from more than one kind of polymer. For example, use of more than one kind of polymer allows sleeve 14 to be formed with a distal remainder including the proximal portion having a durometer of about 70 D to about 80 D.

Referring now also to FIGS. 3–7, system 10 also includes a first or inner balloon 32, a second or outer balloon 34 and an expandable stent 36. The first, or inner, balloon 32 is preferably formed from a non-compliant material, and the outer balloon 34 is preferably formed from a compliant type material.

As use herein, a "non-compliant" material balloon will exhibit a diameter change of about 10 percent or less (preferably 3 to 10 percent) when its internal pressure changes from 4 atmospheres to 13 atmospheres and a "compliant" material balloon will exhibit a diameter change of about 11 percent or more (preferably 11 to 20 percent) when its internal pressure changes from 4 atmospheres to 13 atmospheres.

Each of balloons 32, 34 are preferably formed with a "memory" so that when deflated or depressurized, they will return to a rolled or "folded" state (known as "rewrap") as indicated in the figures. Stent 36 is preferably a non-self deploying or balloon-expandable type stent, such as depicted in U.S. Pat. No. 4,733,665.

FIG. 3 shows the assembly with both balloons deflated, but with the sleeve 14 retracted and with the stent 36 ready for deployment. Lumen 24 is in fluid communication with the interior of inner balloon 32 via a skive 41. Lumen 26 is in fluid communication with the region between inner balloon 32 and the interior of outer balloon 34 via a second skive 43. A first pair of radiopaque marker bands 38, 40 are preferably positioned to indicate the location and extent of first balloon 32 and an anticipated post-deployment location and length of stent 36. A second pair of bands 42, 44 may be used to indicate the location and extent of the second balloon 34 and a predeployed location and length of stent 36. As may be seen in the figures, the first balloon 32 is positioned radially inward of the stent 36 and has a working section 33 having a length 37 substantially equal to the axial length of the stent 36 when the stent is in a deployed condition (as shown in FIGS. 6 and 7) and the second balloon 34 has a working section 35 having a length substantially equal to or greater than the non-deployed length of the stent 36, as indicated most particularly in FIG. 5. It is to be understood that the non-self-deploying stent 36 useful in the practice of the present invention may "shrink" or reduce in axial length by as much as 15 to 20 percent or more (of the non-deployed length) when deployed to the design diameter or condition for the stent. Such axial shrinkage occurs because the filaments or elemental sections of the stent 36 are typically not extensible, but rather move from a generally axial orientation to a more radial (helical) orientation.

Because of this property of the stent, it is useful to define a working section for each balloon in relation to the length of the stent when the balloon is disposed within the stent for expansion against the stent. Thus, the working section of the outer balloon will be substantially equal to the length of a collapsed or non-deployed stent, while the working section of the inner balloon will preferably be substantially equal to the length of the post-deployed or expanded stent, after it is enlarged by inflation of the outer balloon, but before any further radial enlargement by the inner balloon. Stated more generally, the working section of a balloon is preferably about equal to the length of the stent as it exists immediately prior to the stent being acted upon (urged radially outward) by that balloon. Making the outer balloon working section equal to the length of the non-deployed stent will ensure that the stent is deployed along its full axial length, while making the working section of the inner balloon equal to the length of the deployed stent will avoid direct contact between the inner balloon and the vessel during post-deployment expansion of the stent and will cause the inner balloon to fully engage the deployed stent for post-deployment "processing" (i.e., "setting" or further enlargement) of the stent. Because of the higher pressures utilized in post-deployment expansion, direct contact between the inner balloon and the vessel could result in over-expansion of the vessel in the regions beyond the axial ends of the stent if the inner balloon were permitted to be longer than the post-deployment length of the stent. Having the inner balloon substantially shorter than the length of the deployed stent may result in an undesirable condition wherein the stent protrudes into the vessel at one or both ends thereof.

As an example, and not by way of limitation, the stent may be 20 mm long before deployment and 15.4 mm long after deployment. For such a stent, the present invention will preferably have a working section for the inner balloon of 15.4 mm and a working section for the outer balloon of 20 mm or more.

In the practice of the present invention, the stent delivery system is manipulated until the stent is located radially inward of a stenosis in a vessel to be treated, preferably using radiopaque marker bands. The sleeve 14 is then retracted using finger pull 15 until the stent 36 is exposed as shown in FIG. 3. The outer balloon 34 is inflated to deploy the stent, as shown in FIG. 6. The outer balloon 34 is then deflated and the inner or first balloon is then inflated (as shown in FIG. 7) to "set" or fix the stent 36 in place. The inner balloon is then deflated and the stent delivery system (less the stent 36) is removed from the vessel, leaving the stent in place. The outer balloon is preferably of a softer and tougher material than the inner balloon, protecting the inner balloon from damage.

Figure 8:
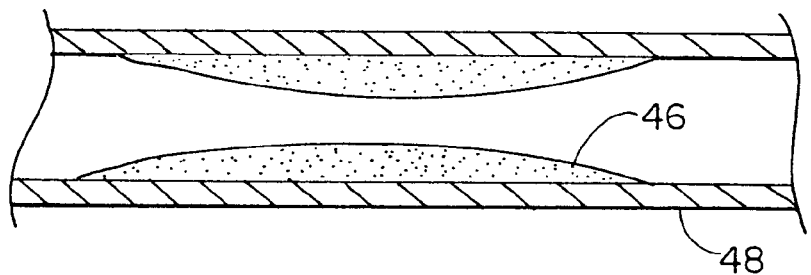
FIG. 8 is a simplified section view of a vessel with a stenosis.
Figure 9:
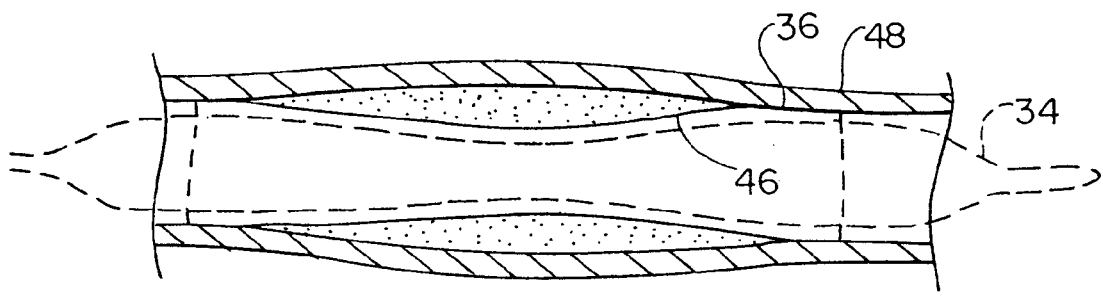
FIG. 9 is a simplified section view of the vessel and stenosis of FIG. 5 with a stent deployed via inflation of the outer balloon corresponding to FIG. 6.
Figure 10:
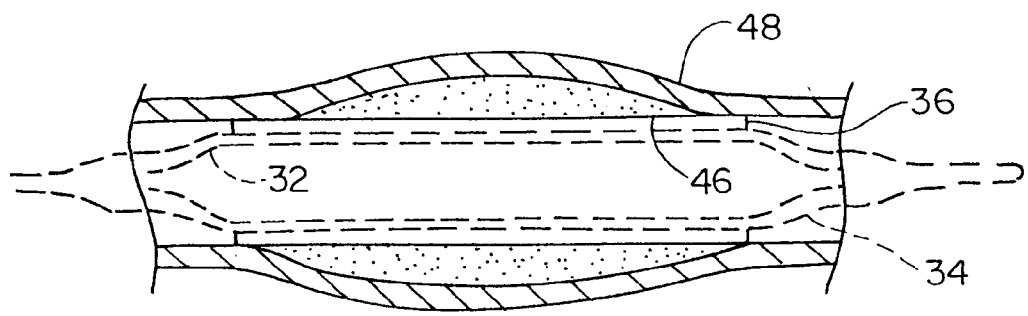
FIG. 10 is a simplified section view of the vessel and stenosis of FIG. 5 with the stent expanded after deployment using the inner balloon corresponding to FIG. 7.

The inner balloon, being non-compliant, will also enable a stenosis enlargement procedure, as illustrated by FIGS. 8, 9, and 10. In FIG. 8, a simplified view of a stenosis 46 interior of a vessel 48 is shown. The stent 36 is shown deployed in FIG. 9. However, even after deployment using the outer balloon 34, the stenosis may protrude at least partially radially into the interior bore of the vessel 48. Inflating the inner balloon 32 will urge the stenosis 46 radially outward, substantially restoring the interior diameter of the stenosis to the diameter of the bore of the vessel, as shown in FIG. 10. Using the inner balloon 32 to accomplish this radial enlargement of the stenosis bore typically will entail higher pressures than used to deploy the stent, and thus will utilize the non-compliant character of the inner balloon to hold the diameter more constant over a greater pressure range than would be the case with a compliant inner balloon. It is to be understood that the outer balloon is preferably used to deploy the stent at relatively low inflation pressures and the inner balloon is preferably used to either "set" or shape the stent using relatively high pressures, but without over-enlarging the radial dimension of the deployed stent. It is to be further understood, however, that post-deployment inflation of the inner, non-compliant balloon 32 will typically result in further, limited, expansion of the stent 36, and consequent similar expansion of the vessel region 48 radially outward of the stent 36. In the practice of the present invention, it may be desirable to utilize a laminated balloon construction, particularly for the inner balloon 32. Such a laminated structure may include an exterior nylon layer, for example, and a PET (polyethylene terepthalate) inner layer, combining the puncture resistance and improved rewrap memory of the nylon with the non-compliant high pressure capability of the PET.

Figure 11:
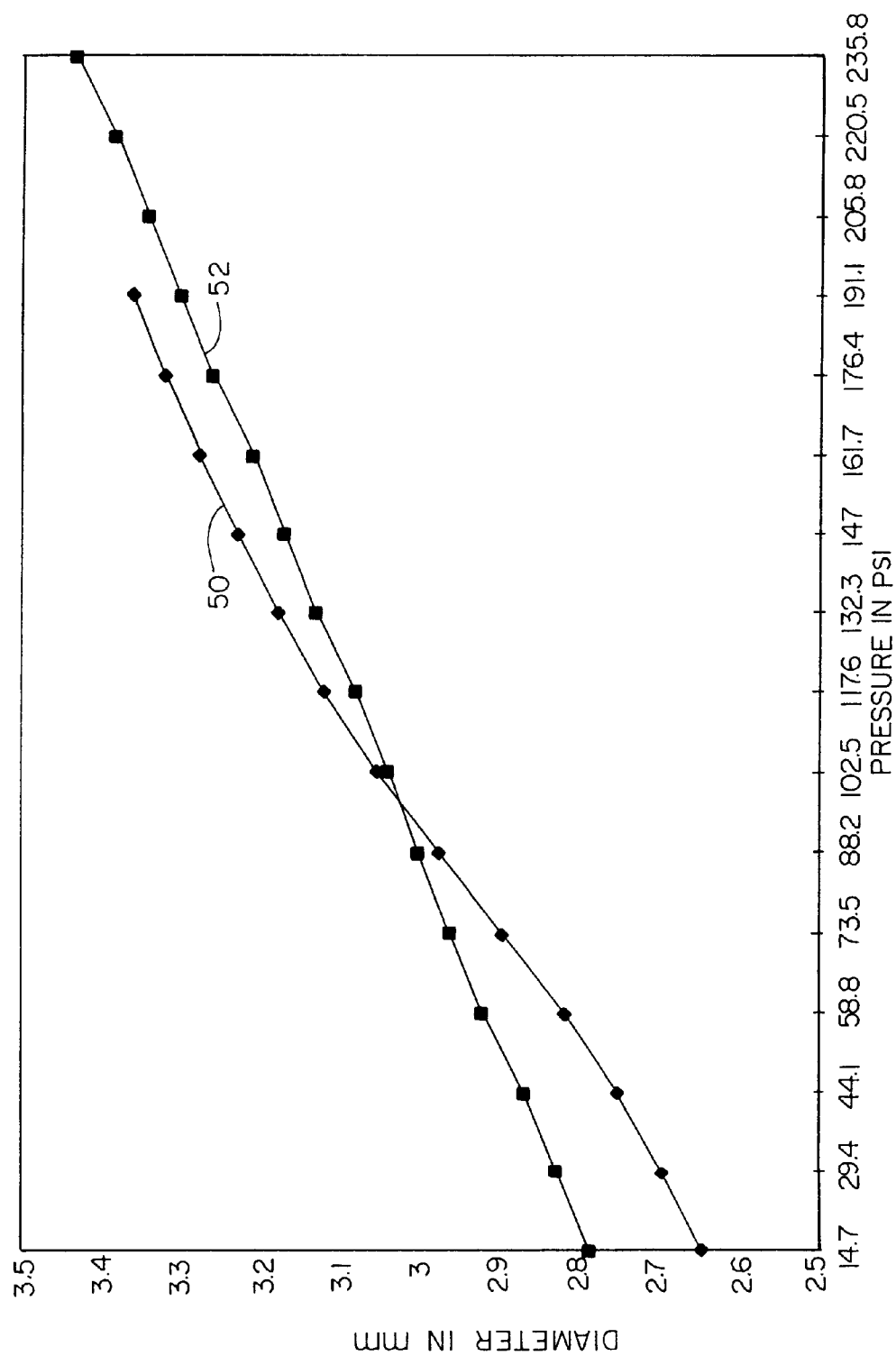
FIG. 11 is a graph of the distention characteristics for certain materials suitable for the outer balloon.
Figure 12:
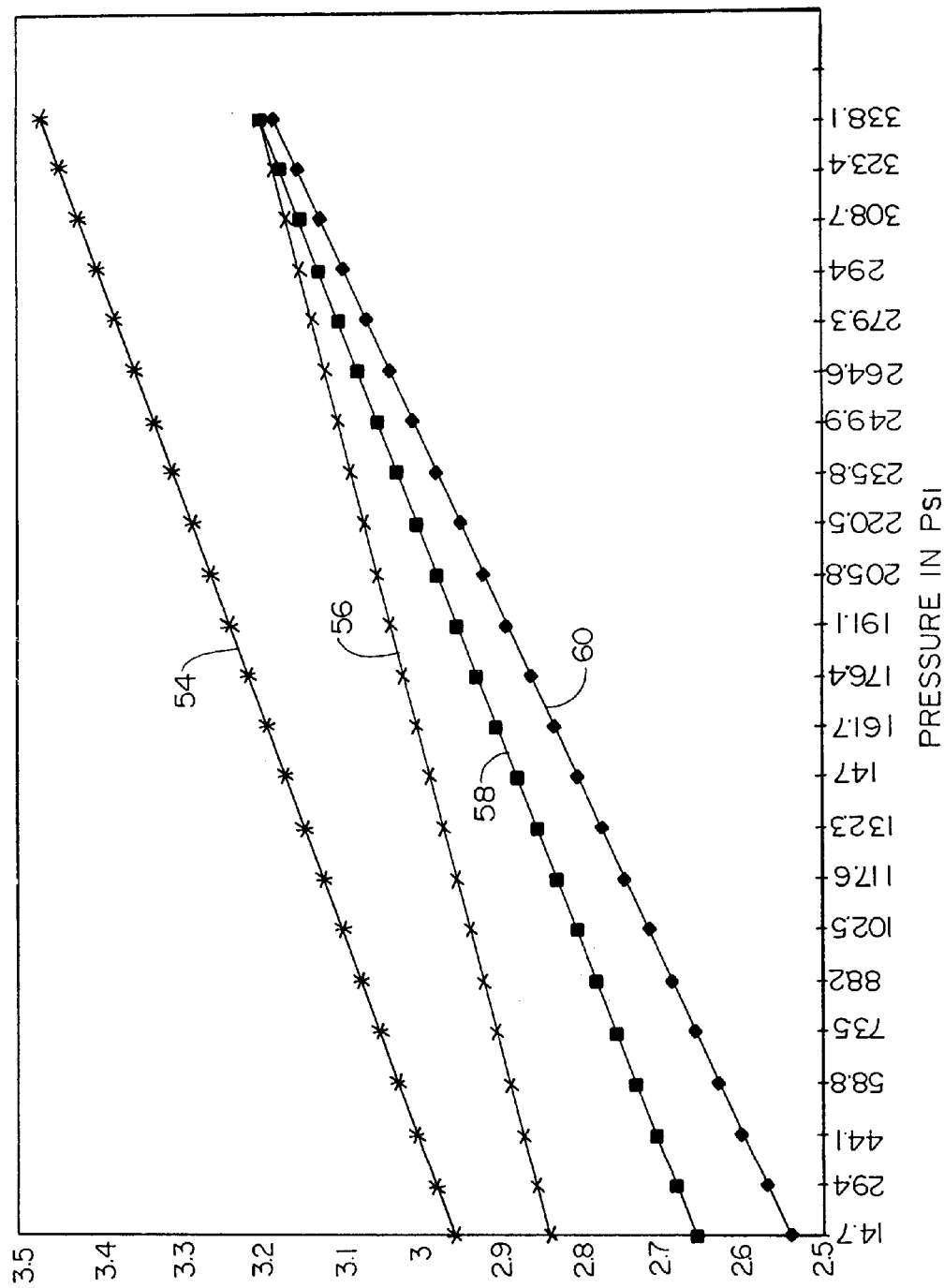
FIG. 12 is a graph of the distention characteristics for certain materials suitable for the inner balloon.

Referring now to FIGS. 11 and 12, the distention curves for various materials for certain compliant and non-compliant balloons may be seen. In FIG. 11, two example compliant materials for the outer balloon are shown. Curve 50 illustrates the diameter change versus pressure for a polyethylene polymer, and curve 52 represents nylon 12. In FIG. 12, various example non-compliant materials are illustrated: curve 54 is for a PET material, and curves 56, 58, and 60 show the distention characteristic for PET/PA 12 laminate construction, (where PE is polyethylene, PET is polyethylene terephthalate, PA refers to a polyamide material and PA12 refers specifically to nylon 12). Curve 56 is for a two layer laminate having an internal PET layer laminated to an external PA layer wherein the PET/PA thickness ratio is 75/25; curve 58 is for 50% PET, 50% PA; and curve 60 is for 25% PET, 75% PA. Suitable wall thicknesses for the PET/PA laminated structure are from about 0.00037" to about 0.0008411" overall. Although the curves shown are for layer ratios of 75/25%, 50/50%, and 25/75%, it is to be understood that other layer thickness ratios (such as 60% PET/40% PA) are suitable as well. For illustrative purposes, the following table gives approximate percentage diameter changes over a 4–13 atmosphere pressure range for various representative polymeric materials that are commercially available:

TABLE I

| Compliant | % | Non-compliant | % |
|---|---|---|---|
| PE | 18 | PET | 7 |
| Nylon 12 | 13 | 75% PET/25% PA12 | 5 |
| | | 50% PET/50% PA12 | 8 |
| | | 25% PET/75% PA12 | 10 |

Generally a variety of polymer types could be used as either the compliant or non compliant material. One skilled in the art could formulate a polymer type so that the polymer would have the right characteristics. Examples of the polymer types that could be used include the below listed materials. Suitable materials for the balloons are as follows.

Various nylons (depending upon how they are formulated) can be incorporated into either the compliant or non-compliant balloon (alone or in a blend or in a laminated structure), specifically: Grilamid L25 (available from EMS of Zurich, Switzerland); Vestamide 2101 F or Vestamide 1801 F (available from Huls America Inc. of Piscataway, N.J.).

For the non-compliant material, several applicable PET homopolymers are: ICI 5822C (available from ICI Americas, P.O. Box 630, Cardell plant, Fayetteville, N.C., 28302) and Shell Traytuf 1006.

For the compliant material, the following are representative of acceptable polymers:

| | Source |
|---|---|
| Thermoplastic Polyether Blockamide<br>7033 Pebax<br>6333 Pebax<br>5533 Pebax | Elf Atochem |
| Rigid Polyurethane<br>2510 Isoplast | Ashland |
| Polyester Elastomer<br>72D Hytrel HTR8276<br>82D Hytrel HTR8280<br>63D Hytrel HTR8279<br>45D Hytrel HTR8278 | DuPont |
| Polyurethane<br>63 D Pellethane<br>55 D<br>75 D | Dow |
| Polyethylene<br>2247A Dowlex<br>2938 Dowlex | Dow |

Although a number of materials have been listed above, it is to be understood that the compliant and non-compliant balloons can be prepared from a wide range of thermoplastic and or thermosetting polymer resins having the desired compliant or non-compliant characteristics.

A method of using the stent deployment device 10 is as follows. The stent deployment device 10 is inserted into a vessel and manoeuvered to position the distal region at a treatment site. The sheath 14 is then retracted such that the stent 36 is presented to the treatment site. The outer balloon 34 is then inflated to deploy the stent 36 and then deflated to rewrap the outer balloon. The inner balloon is then inflated to expand or "set" the stent in the vessel at the treatment site, after which the inner balloon is deflated to rewrap the inner balloon, and the device 10 is eventually withdrawn from the vessel.

The invention is not to be taken as limited to all of the details thereof as modifications and variations thereof may be made without departing from the spirit or scope of the invention.

What is claimed is:

1. A medical device comprising:
   a) a catheter having a proximal portion and a distal portion;
   b) a stent disposed about the distal portion of the catheter, the stent radially expandable between a reduced-diameter, non-deployed state at which the stent has a non-deployed length and an increased-diameter, deployed state at which the stent has a deployed length which is less than the non-deployed length;
   c) a relatively non-compliant, discrete inner balloon disposed about the distal portion of the catheter between the catheter and the stent and having an inner balloon working section length at least substantially equal to the deployed length of the stent;
   d) a relatively compliant, discrete outer balloon disposed about the distal portion of the catheter between the inner balloon and the stent and having an outer balloon working section length which is greater than the inner balloon working section length and equal to or greater than the non-deployed length of the stent; and
   e) inflation means for selectively inflating the inner and outer balloons to radially-expand the stent to the deployed state.

2. The device of claim 1 wherein the material of the inner balloon has a compliance of less than about ten percent.

3. The device of claim 2 wherein the material of the inner balloon is polyethylene terephalate.

4. The device of claim 1 wherein the material of the outer balloon has a compliance of greater than about eleven percent.

5. The device of claim 4 wherein the material of the outer balloon is nylon.

6. The device of claim 4 wherein the material of the outer balloon is polyethylene.

7. The device of claim 1 wherein the stent has a pre-deployed length about the same as a length of the working section of the outer balloon.

8. The device of claim 1 wherein the length of the stent is within about ten percent of a length of the working section of the inner balloon.

9. The device of claim 8 wherein the stent is a non-self deploying type stent.

10. The device of claim 1 further comprising:
    f) a sheath disposed about the stent for retaining the stent and axially retractable to release the stent.

11. The device of claim 10 wherein the sheath extends from the distal portion to at least near the proximal portion of the catheter.

12. The device of claim 1 wherein the inflation means comprises:
    f) a first lumen extending between the proximal and distal portions of the catheter and in fluid communication with the inner balloon; and
    g) a second lumen extending between the proximal and distal portions of the catheter and in fluid communication with the outer balloon such that the inner and outer balloons can be selectively inflated by applying fluid pressure to the respective lumen at the proximal end of the catheter.

13. The device of claim 1 wherein the catheter further comprises a central lumen adapted to be received over a guide wire.

14. The device of claim 1 wherein the catheter further comprises a tapered tip at an end of the distal portion thereof.

15. The device of claim 1 further comprising:
    f) a first pair of radiopaque bands positioned at respective first and second ends of the inner balloon.

16. The device of claim 15 further comprising:
    g) a second pair of radiopaque bands positioned at respective first and second ends of the outer balloon.

17. The device of claim 16 wherein the inner balloon is less compliant than the outer balloon.

18. The medical device of claim 1 wherein the inner balloon working section length is substantially equal to the deployed length of the stent.

19. A medical device comprising:
    a) a catheter having a proximal portion and a distal portion;
    b) a inner balloon having a working section characterized by an axial length and disposed about the distal portion of the catheter, the inner balloon having an inner balloon compliance;
    c) a outer balloon having a working section characterized by an axial length greater than the axial length of the working section of the inner balloon and disposed about the inner balloon at the distal portion of the catheter the outer balloon having an outer balloon compliance which is greater than the inner balloon compliance;
    d) a stent disposed about the inner and outer balloons and having a non-deployed length less than or equal to the axial length of the working section of the outer balloon and a deployed length substantially equal to the axial length of the working section of the inner balloon and e) inflation means for selectively inflating the inner and outer balloons to radially-expand the stent to the deployed state.

20. A method of using a stent deployment device having a stent deployment balloon and a stent expansion balloon comprising the steps of:

a) inserting the stent deployment device into a vessel wherein the device has a inner balloon disposed about a distal region thereof and having an inner balloon compliance, a outer balloon disposed about the inner balloon and having an outer balloon compliance which is greater than the inner balloon compliance, a stent disposed about the outer balloon, and a sheath disposed about the stent;

b) maneuvering the device to position the distal region at a treatment site;

c) retracting the sheath such that the stent is presented to the treatment site;

d) inflating the outer balloon to deploy the stent;

e) inflating the inner balloon along substantially the full axial length of the deployed stent to further expand and set the stent; and f) withdrawing the device from the vessel.

21. The method of claim 20 further comprising an additional step between steps d) and e) of:

d1) deflating the outer balloon.

22. The method of claim 21 further comprising an additional step between steps e) and f) of:

e1) deflating the inner balloon.

23. The method of claim 19 wherein the step of inserting the deployment device includes inserting a device having an outer balloon having a length which is at least as long as the full axial length of the non-deployed stent, and wherein the inner balloon is shorter than the outer balloon and at least as long as the full axial length of the deployed stent.

* * * * *

UNITED STATES PATENT AND TRADEMARK OFFICE
CERTIFICATE OF CORRECTION

PATENT NO. : 5,980,531
DATED : November 9, 1999
INVENTOR(S) : Goodin et al.

It is certified that error appears in the above-identified patent and that said Letters Patent is hereby corrected as shown below:

>Column 8, line 11, delete "19" and insert therefor --20--; lines 12 and 13, delete "having an outer balloon having" and insert therefor --wherein the outer balloon has--

Signed and Sealed this

Twenty-fourth Day of October, 2000

Attest:

Q. TODD DICKINSON

*Attesting Officer*  *Director of Patents and Trademarks*